US00PP29786P3

(12) United States Plant Patent
Nebelmeir

(10) Patent No.: US PP29,786 P3
(45) Date of Patent: Oct. 30, 2018

(54) ***PORTULACA* PLANT NAMED 'LAZPRT1705'**

(50) Latin Name: ***Portulaca umbraticola* Kunth**
Varietal Denomination: LAZPRT1705

(71) Applicant: Lazzeri Società Agricola a R.L., Sabaudia (LT) (IT)

(72) Inventor: Johannes Sebastian Nebelmeir, Marling (IT)

(73) Assignee: Lazzeri Società Agricola a R.L., Sabaudia (LT) (IT)

( * ) Notice: Subject to any disclaimer, the term of this patent is extended or adjusted under 35 U.S.C. 154(b) by 0 days.

(21) Appl. No.: 15/732,250

(22) Filed: Oct. 13, 2017

(65) Prior Publication Data

US 2018/0110172 P1 Apr. 19, 2018

Related U.S. Application Data

(60) Provisional application No. 62/496,346, filed on Oct. 14, 2016.

(51) Int. Cl.
*A01H 5/02* (2018.01)

(52) U.S. Cl.
USPC ..... Plt./471
CPC ..... *A01H 5/02* (2013.01)

(58) Field of Classification Search
USPC ..... Plt./471
See application file for complete search history.

*Primary Examiner* — Annette H Para
(74) *Attorney, Agent, or Firm* — The Webb Law Firm

(57) ABSTRACT

A new and distinct *portulaca* plant having red and white bicolored, star-patterned flowers with an intermediate yellow zone between.

4 Drawing Sheets

Botanical classification: *Portulaca umbraticola* Kunth.
Varietal denomination: 'LAZPRT1705'.

BACKGROUND OF THE INVENTION

The present invention comprises a new and distinct cultivar of *portulaca* plant known by the varietal name 'LAZPRT1705'. The new variety is the result of a planned breeding program with the purpose of developing a *portulaca* variety with a novel bicolored flower pattern. 'LAZPRT1705' was created via a cross conducted in the Summer of 2010 in Merano, Italy between an unnamed and unpatented *Portulaca umbraticola* Kunth variety from the breeder's proprietary breeding line 07/244-1 (female parent) and an unnamed and unpatented *Portulaca umbraticola* Kunth variety (male parent) having cream and red bicolored, star-patterned flowers. The new variety was selected in the Spring of 2011 in Merano, Italy and the first asexual reproduction of the new variety was conducted by cuttings in the Spring of 2012 in Merano, Italy. 'LAZPRT1705' has been trial and field tested and has been found to retain its distinctive characteristics and remain true to type through successive propagations. The present invention has not been evaluated under all possible environmental conditions. The phenotype may vary with variations in environment without a change in the genotype of the plant.

'LAZPRT1705' is similar to its female parent in its bicolored star flower pattern, but the pattern of 'LAZPRT1705' has better contrast (red and white colors with an intermediate yellow zone versus red and cream colors) and a more stable expression than its female parent. Further, 'LAZPRT1705' exhibits better branching than its female parent. When 'LAZPRT1705' is compared to *Portulaca umbraticola* Kunth 'LAZPRT1609', also referred to as "DUNA COLORBLAST Mango Mojito" (unpatented), the varieties are similar in that they both exhibit a bicolored flower pattern. However, 'LAZPRT1705' has red and white colored flowers that have a stronger color contrast than the red and whitish yellow colored flowers of 'LAZPRT1609'. Further, 'LAZPRT1705' has larger and more open flowers than 'LAZPRT1609'.

The following traits distinguish 'LAZPRT1705' as a new and distinct cultivar from other *portulaca* varieties known to the breeder:

1. Red and white bicolored star flower pattern with an intermediate yellow zone present;
2. Good growth habit and vitality;
3. Freely branching with pinching not necessary; and
4. Excellent heat and drought tolerance.

DESCRIPTION OF THE DRAWINGS

The accompanying photographic drawings taken at approximately 4 months of age illustrate the new variety, with the color being as nearly true as is possible with color illustrations of this type.

DESCRIPTION OF THE PLANT

Figure 1:
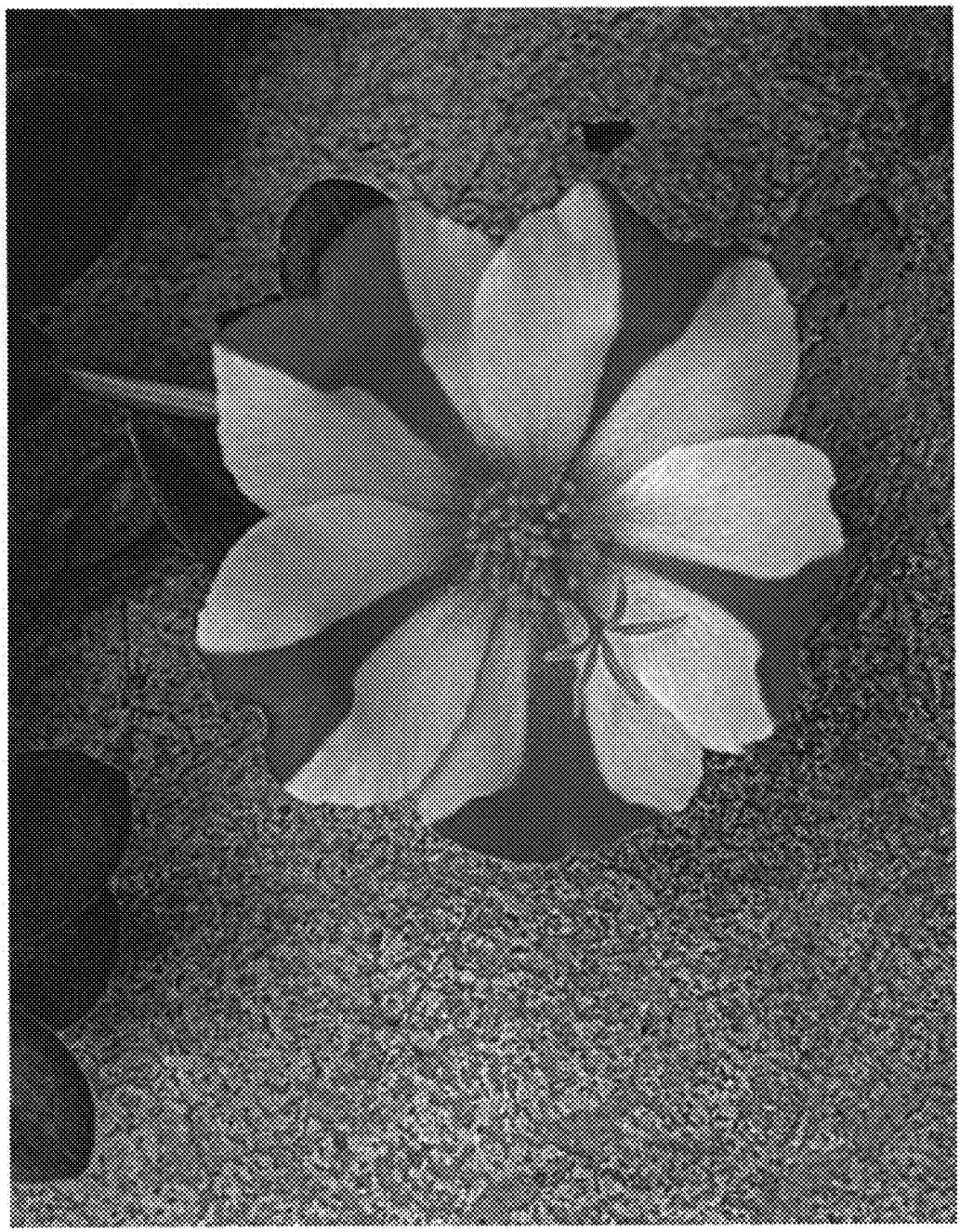
FIG. 1 shows a close-up view of a flower of the new variety.
Figure 2:
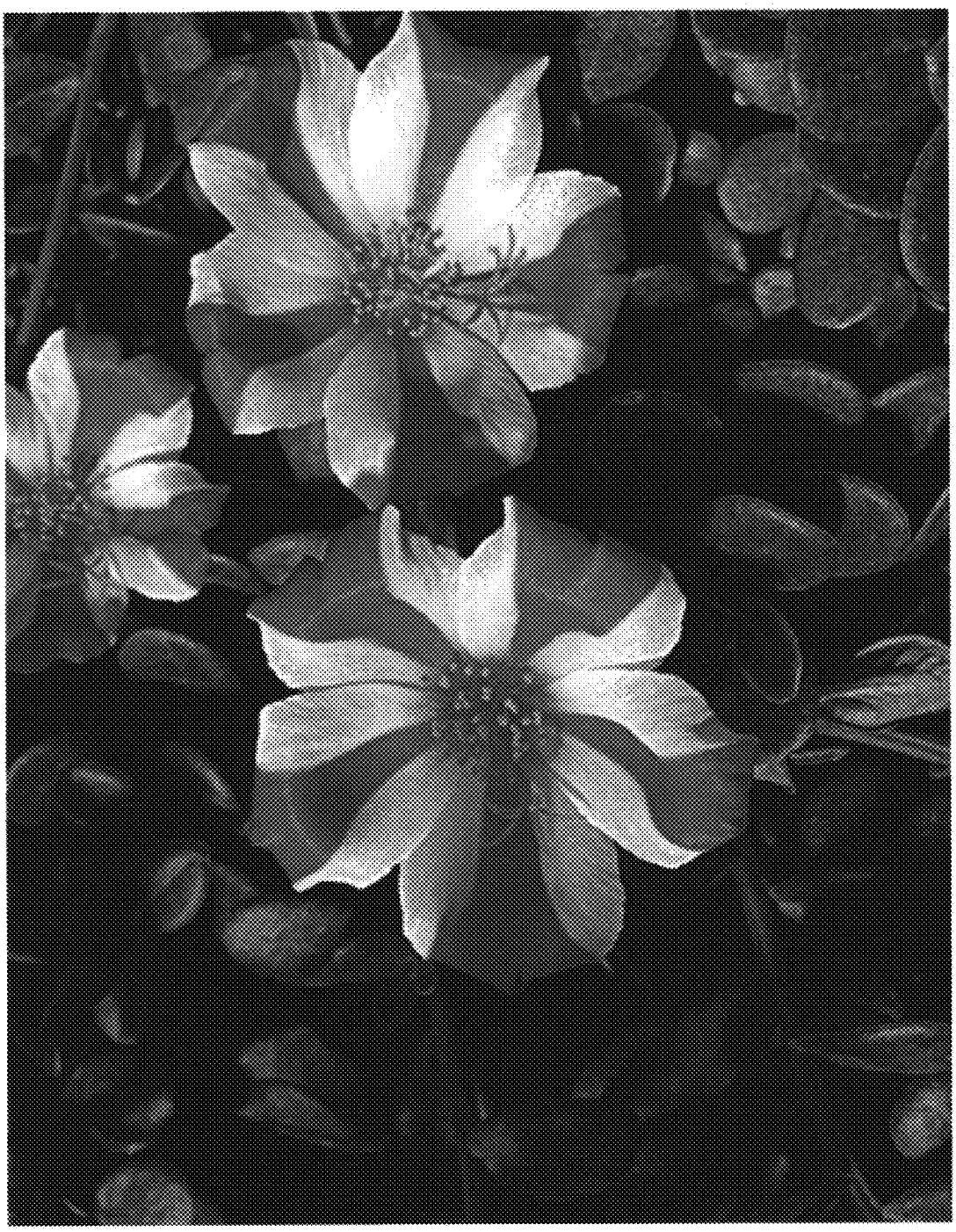
FIG. 2 shows a close-up view of flowers of the new variety.
Figure 3:
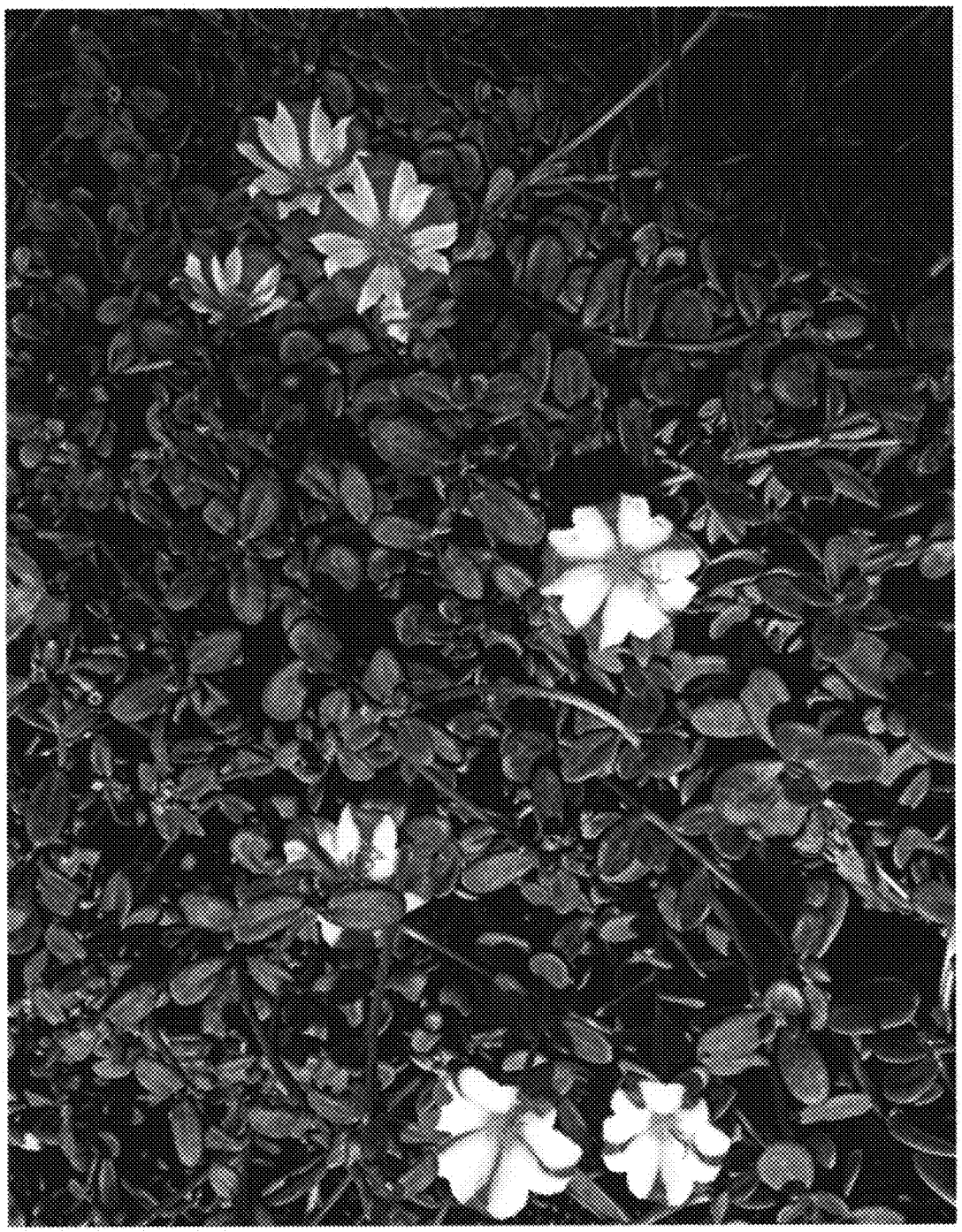
FIG. 3 shows close-up view of a plant of the new variety.
Figure 4:
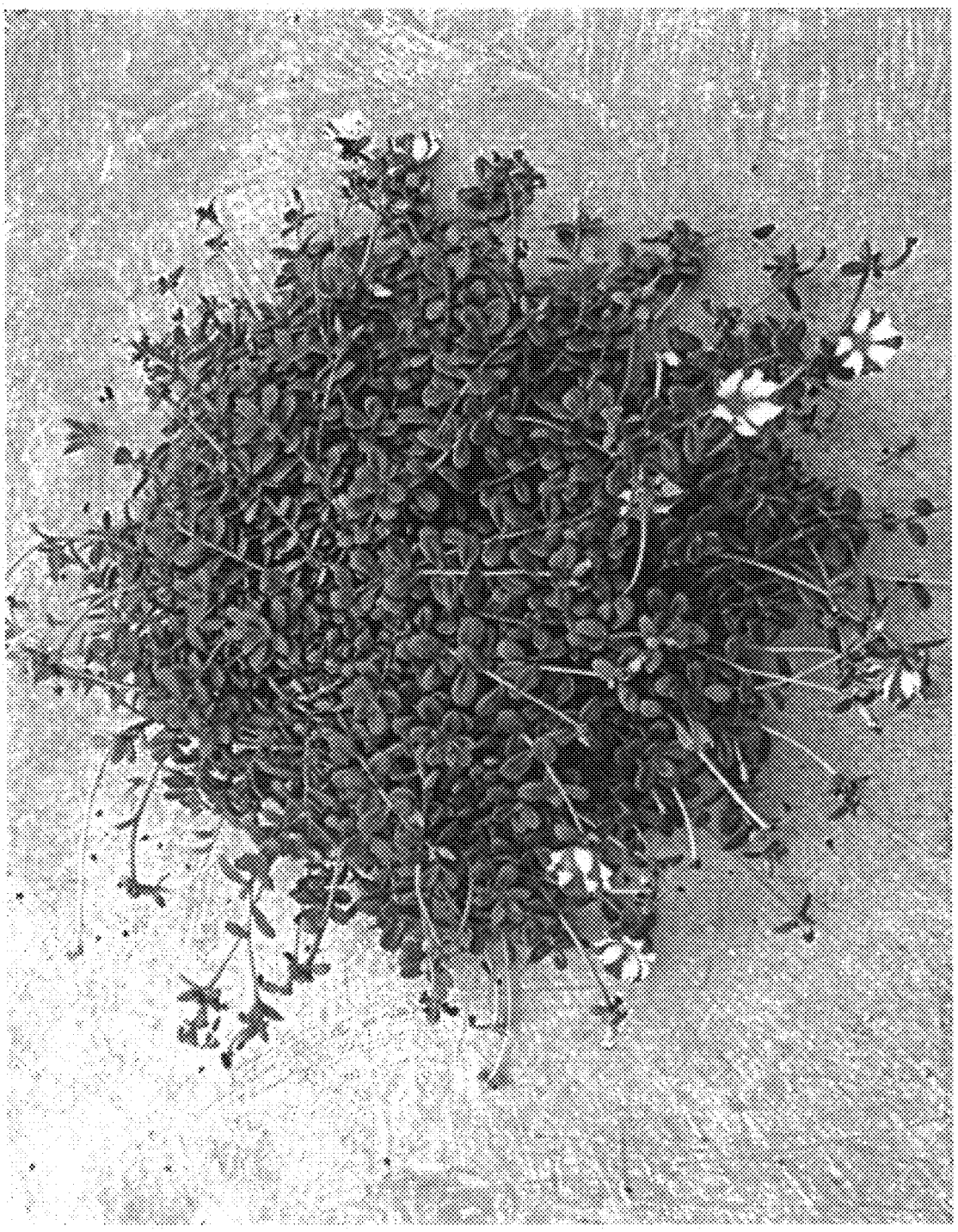
FIG. 4 shows a view of a plant of the new variety.

The following detailed description sets forth the characteristics of the new variety. The data which defines these characteristics were collected in Merano, Italy in the Summer. Plants of the new variety were grown in Merano, Italy in a glass greenhouse under full natural light levels of 60-70 klx in 13 cm pots with a moderate watering regimen, an average day temperature of 18° C., and an average night temperature of 12° C. The color readings and measurements were taken indoors in a greenhouse under natural light on approximately 4 month old plants grown in containers. Color references are primarily to The 1995 R.H.S. Colour Chart of The Royal Horticultural Society of London.

PLANT

Plant type and use: Annual plant for bed and balcony use.
Number of days to initiate roots (summer): 10 days at an average of 22° C.
Number of days to produce a rooted young plant (summer): 24 days.
Number of days to initiate roots (winter): 14 days at an average of 15° C.
Number of days to produce a rooted young plant (winter): 28 days.
Time to finish a flowering plant: Approximately 8-10 weeks.
Overall plant shape and growth habit: Compact and creeping.
Plant height: Approximately 10 cm.
Plant diameter: Approximately 50 cm.
Growth rate: Rapid.
Plant vigor: High.
Roots:
- *Density*.—Moderate.
- *Branching*.—Freely.
- *Thickness*.—Thin.
- *Texture*.—Fibrous.
- *Color*.—Pale creamy white.

Branching:
- *Habit*.—Freely branching from every node without pinching required.
- *Basal branching*.—Present.
- *Lateral branches*.—Number: Numerous. Length: About 25 cm. Diameter: 3-4 mm. Internode length: 2-20 mm.

Stem:
- *Appearance*.—Almost round with lateral ridges.
- *Aspect/angle*.—Monopodial.
- *Strength*.—4 mm.
- *Outer color*.—148B, with strong underlying betalain coloration present.
- *Core color*.—185B when cut open.
- *Bark color*.—No bark formed.
- *Pubescence*.—None present.
- *Texture*.—Smooth and glabrous; succulent.

Foliage:
- *Appearance*.—Alternate and simple.
- *Shape*.—Obovate.
- *Apex*.—Younger leaves are slightly acute; older leaves are rounded.
- *Base*.—Obtuse.
- *Margin*.—Entire.
- *Length range*.—16-22 mm.
- *Width range*.—9-13 mm.
- *Texture*.—Upper surface: Smooth, glabrous, succulent. Lower surface: Pearly, glabrous, succulent.
- *Pubescence*.—None present.
- *Color*.—Young leaves: Upper surface: 137B. Lower surface: 148B. Mature leaves: Upper surface: Generally 147A; with full sun exposure, a very slight shade of 185B betalain coloration may be seen on the margins. Lower surface: Generally 147B; with full sun exposure, a very slight shade of 185B betalain coloration may be seen on the margins.
- *Veins*.—Venation type: Pinnate, almost only midrib is visible. Color: Upper surface: 147B. Lower surface: 146B.
- *Petiole*.—Length: 1-2 mm. Diameter: 1-2 mm. Texture: Glabrous and succulent on both surfaces. Color: Upper surface: 146B. Lower surface: 146C.
- *Stipule*.—None present.
- *Leaf axil*.—Fine, yellowish-white hairs are present in the axillary area that are 1-2 mm in length.

FLOWERS

Buds:
- *Number of buds per plant*.—Numerous.
- *Number of buds per lateral stem*.—Usually 3-5 are visible at differing developmental stages.
- *Shape of individual bud*.—Ovoid.
- *Length of individual bud*.—Approximately 13 mm one day before flowering.
- *Width of individual bud*.—Approximately 6 mm one day before flowering.
- *Bud color*.—146B, with medium betalain coloration.

Natural flowering season at specified location: From mid-Spring to mid-Autumn in Merano, Italy.
Time to flowering: 6-8 weeks after potting.
Inflorescence number per lateral stem: One terminal inflorescence per lateral stem; usually from 1 or 2, sometimes 3, open at one time per mature lateral stem.
Number of flowers per inflorescence: Recurrently flowering with about 15-30 flowers per inflorescence in a single season.
Inflorescence:
- *Description*.—Clustered cyme with sessile flowers.
- *Height*.—Average of 2-3 cm.
- *Width*.—Average of 5 cm.

Flower:
- *Arrangement*.—Terminal, surrounded by a whorl of usually 3 leaves.
- *Description*.—Single, rotate flowers that face upward; not persistent; self-cleaning.
- *Lastingness of an individual flower on the plant*.—Ephemeral flowers that last from about 1-3 days on the plant.
- *Lastingness of a cut flower*.—Not applicable.
- *Shape*.—Pentagonal, rotate, single.
- *Diameter*.—About 40-50 mm.
- *Depth (height)*.—About 15-20 mm.
- *Aspect*.—Upright.
- *Fragrance*.—None present.

Petals:
- *Appearance*.—Distinct and unfused.
- *Arrangement*.—Whorl.
- *Number per flower*.—5.
- *Shape*.—Obovate.
- *Apex*.—Cordate.
- *Base*.—Square.
- *Margin*.—Generally entire; slightly serrate toward the apex.
- *Length*.—About 22 mm.
- *Width*.—About 18 mm.
- *Texture (both surfaces)*.—Smooth, glabrous.
- *Color*.—Upper surface (when opening): 45A to 46B (red area), 9A to 12B (intermediate yellow area), and 155A to 11D (white area). Lower surface (when opening): 45B to 45C (red area) and 155A to 11D (white area). Upper surface (fully opened): 45A to 46B (red area), 9A to 12B (intermediate yellow area), and 155A to 11D (white area). Lower surface (fully opened): 45B to 45C (red area) and 155A to 11D (white area). Both surfaces (shriveled after opening): 46A to 53A.

Petaloid description: None present.
Sepals:
*Number per flower*.—Two.
*Appearance*.—Opposite.
*Arrangement*.—Free.
*Shape*.—Deltoid.
*Apex*.—Acute.
*Base*.—Truncate.
*Margin*.—Entire.
*Length*.—About 11 mm.
*Width*.—About 8 mm.
*Texture*.—Upper surface: Smooth, glabrous. Lower surface: Smooth, glabrous, leathery.
*Mature color*.—Upper surface: 147C. Lower surface: 146B, with medium betalain present.
*Calyx*.—Appearance: Beaker-shaped with 2 lateral ridges. Length: About 4 mm. Diameter: About 6 mm.
Peduncle description: None present (sessile flowers).
Pedicel description: None present.
Reproductive organs:
Stamens:
*Number* (*per flower*).—About 50-60.
*Filament*.—Length: About 5-6 mm. Color: Orange.
*Anthers*.—Shape: Ellipsoid. Length: 1 mm. Color: 25B.
*Pollen*.—Color: 24A. Amount (generally): Average.
Pistils:
*Number*.—One, parted into 5-6 tentacle-shaped stigmas.
*Length*.—About 10 mm.
*Style*.—Length: About 10 mm. Color: Orange-red.
*Stigma*.—Shape: Elongated and tentacle-shaped. Color: Orange-red.
*Ovaries*.—Not visible.

SEEDS/FRUIT

Seeds:
*Number per flower*.—Up to approximately 40.
*Diameter*.—About 1 mm.
*Color*.—Greyish black.
Fruit:
*Quantity per lateral branch*.—Each flower produces one seed pod.
*Amount of fruit per plant*.—Numerous.
*Length*.—About 4 mm.
*Diameter*.—About 6 mm.
*Color*.—Light green to green.
*Texture*.—Succulent to leathery.
*Taste*.—Not applicable.
*Number of days to ripening*.—7-10.

GENERAL

Disease/pest resistance or susceptibility: None observed.
Cold temperature tolerance: Tolerant to long term exposure of approximately 10° C.; tolerant to short term exposure of approximately 5° C. (under a dry water regimen).
Hot temperature tolerance: Excellent, with no observed upper limit to date.
Drought tolerance: Excellent.
Rain tolerance: Good, may suffer from prolonged water exposure in soil with poor drainage.
Wind tolerance: Good, quickly recovers from wind damage as new flowers open on a daily basis.
Keeping quality: The entire plant performs very well throughout an entire Summer with the continuous rotation of blooming ephemeral flowers.

I claim:

1. A new and distinct variety of *portulaca* plant, as is herein illustrated and described.

* * * * *